(12) United States Patent
Wu et al.

(10) Patent No.: US 9,848,796 B2
(45) Date of Patent: Dec. 26, 2017

(54) METHOD AND APPARATUS FOR CONTROLLING MEDIA PLAY DEVICE

(71) Applicant: Xiaomi Inc., Beijing (CN)

(72) Inventors: Ke Wu, Beijing (CN); Xinyu Liu, Beijing (CN)

(73) Assignee: Xiaomi Inc., Beijing (CN)

( * ) Notice: Subject to any disclaimer, the term of this patent is extended or adjusted under 35 U.S.C. 154(b) by 0 days.

(21) Appl. No.: 15/135,245

(22) Filed: Apr. 21, 2016

(65) Prior Publication Data

US 2017/0049350 A1   Feb. 23, 2017

(30) Foreign Application Priority Data

Aug. 21, 2015   (CN) .......................... 2015 1 0518405

(51) Int. Cl.
*G06F 17/00*   (2006.01)
*A61B 5/0476*   (2006.01)
(Continued)

(52) U.S. Cl.
CPC ............ *A61B 5/0476* (2013.01); *G05B 15/02* (2013.01); *G06F 3/015* (2013.01); *G06F 3/165* (2013.01);
(Continued)

(58) Field of Classification Search
CPC ....... A61B 5/0476; G05B 15/02; G06F 3/015; G06F 3/165; H04N 5/4403; H04N 2005/4428; H04N 2205/4428
(Continued)

(56) References Cited

U.S. PATENT DOCUMENTS 4,013,068 A * 3/1977 Settle ................... A61B 5/0476
340/573.1
5,813,993 A   9/1998 Kaplan et al.
(Continued)

FOREIGN PATENT DOCUMENTS

CN   102016757 A   4/2011
CN   102737677 A   10/2012
(Continued)

OTHER PUBLICATIONS

International Search Report dated May 16, 2016 in PCT/CN2015/099052 (previously filed, submitting English language translation only).
(Continued)

*Primary Examiner* — Hemant Patel
(74) *Attorney, Agent, or Firm* — Oblon, McClelland, Maier & Neustadt, L.L.P.

(57) ABSTRACT

The present disclosure is related to a play control method, apparatus and terminal. The method comprises: acquiring brain wave information of a user; and controlling an electronic device based on the brain wave information. When the embodiments of this disclosure are applied, by acquiring brain wave information of a user and controlling an electronic device based on the brain wave information, the state of the user can be reflected through the brain wave information; accordingly, effective control of the user's needs can be realized through the brain wave information without any triggering operation by the user, thereby enhancing the user experience and improving the intelligence level of electronic device.

15 Claims, 7 Drawing Sheets

(51) Int. Cl.
*G06F 3/01* (2006.01)
*G05B 15/02* (2006.01)
*G06F 3/16* (2006.01)
*H04N 5/44* (2011.01)

(52) U.S. Cl.
CPC ... *H04N 5/4403* (2013.01); *H04N 2005/4428* (2013.01)

(58) Field of Classification Search
USPC .......................................................... 700/94
See application file for complete search history.

(56) References Cited

U.S. PATENT DOCUMENTS

| | | | | |
|---|---|---|---|---|
| 8,797,331 | B2* | 8/2014 | Sano | G06T 13/40 345/474 |
| 9,005,101 | B1 | 4/2015 | Van Erlach | |
| 2007/0048707 | A1 | 3/2007 | Caamano et al. | |
| 2008/0177197 | A1* | 7/2008 | Lee | A61B 5/165 600/545 |
| 2008/0281221 | A1 | 11/2008 | Greco et al. | |
| 2009/0187114 | A1* | 7/2009 | Morikawa | G06F 3/015 600/545 |
| 2009/0292657 | A1 | 11/2009 | Jung et al. | |
| 2010/0004556 | A1* | 1/2010 | Adachi | A61B 5/0476 600/544 |
| 2010/0137734 | A1 | 6/2010 | Digiovanna et al. | |
| 2010/0191140 | A1* | 7/2010 | Terada | A61B 5/04842 600/544 |
| 2010/0240458 | A1 | 9/2010 | Gaiba et al. | |
| 2010/0304864 | A1 | 12/2010 | Johnson et al. | |
| 2012/0075530 | A1 | 3/2012 | Miyazaki et al. | |
| 2012/0226185 | A1* | 9/2012 | Chung | A61B 5/0476 600/544 |
| 2012/0245713 | A1 | 9/2012 | Chen et al. | |
| 2014/0277582 | A1* | 9/2014 | Leuthardt | A61N 1/36003 623/25 |
| 2015/0091791 | A1* | 4/2015 | Segal | G06F 3/015 345/156 |
| 2015/0377574 | A1* | 12/2015 | Cooke | F41A 17/063 42/70.11 |

FOREIGN PATENT DOCUMENTS

| | | |
|---|---|---|
| CN | 103414908 A | 11/2013 |
| CN | 104376855 A | 2/2015 |
| CN | 104798077 A | 7/2015 |
| CN | 105163180 A | 12/2015 |
| JP | 03-155832 A | 7/1991 |
| JP | 10-262943 A | 10/1998 |
| JP | 2005347990 | 12/2005 |
| KR | 10-1498812 B1 | 3/2015 |
| RU | 2 406 554 C1 | 12/2010 |
| RU | 122 516 U1 | 11/2012 |
| WO | WO 2008/145957 A2 | 12/2008 |
| WO | WO 2009/037654 A2 | 3/2009 |
| WO | WO 2014/102722 A1 | 7/2014 |

OTHER PUBLICATIONS

Extended European Search Report dated Jan. 9, 2017 in Patent Application No. 16184571.4.

Combined Office Action and Search Report dated Feb. 27, 2017 in Russian Application No. 2016134775/07 (054302) with partial English translation and English translation of Categories of Documents.

International Search Report and Written Opinion of the International Searching Authority dated May 16, 2016 in PCT/CN2015/099052 (with English translation of categories of cited documents).

* cited by examiner

METHOD AND APPARATUS FOR CONTROLLING MEDIA PLAY DEVICE

This application claims priority of the Chinese Patent Application No. 201510518405.9, filed on Aug. 21, 2015, which is incorporated herein by reference in its entirety.

TECHNICAL FIELD

The present disclosure is related to the field of communication technology, and more particularly, to a play control method, apparatus and terminal.

BACKGROUND

With rapid development of science and technology of electronics and internet technology, play devices are more and more widely used in people's daily life, such as computers, tablet computers, televisions, mobile phones, personal stereos, hand-held readers and the like. Take televisions as an example, when TV programs are played on TVs, in the related arts, only when receiving control commands triggered by triggering operations by users, will TVs execute control response, such as switching TV programs, pause playing, reducing sound volume etc. When users do not perform triggering operations, it is hard for play devices such as TVs to effectively respond to user's play needs. As a result, the user experience is poor and the intelligence level of play devices is low.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Aspects of the disclosure provide a method for controlling an electronic device. The method includes acquiring brain wave information of a user who is associated with the electronic device, and controlling the electronic device based on the brain wave information.

To acquire the brain wave information of the user who is associated with the electronic device, in an example, the method includes detecting an object being in touch with a sensor device, determining whether the object is the user and acquiring the brain wave information of the user when the object is the user.

To determine whether the object is the user, the method includes receiving touch attributes of the object that is in touch with the sensor device, determining whether at least one of the touch attributes of the object meets a preset condition, and determining that the object that is in touch with the sensor device is the user when the at least one of the touch attributes meets the preset condition.

To determine whether the at least one of the touch attributes of the object meets the preset condition, in an example, the method includes when a shape of the object detected by a built-in area sensor in the sensor device matches with a preset shape, determining that the detected shape meets the corresponding preset condition. In another example, the method includes when a temperature of the object detected by a built-in temperature sensor in the sensor device matches with a preset temperature, determining that the detected temperature meets the corresponding preset condition. In another example, the method includes when a pressure of the object is detected by a built-in pressure sensor, an area of the object is detected by the built-in area sensor, and a ratio of the pressure to the area matches with a preset density, determining that the detected pressure and area meet the corresponding preset condition.

To acquire the brain wave information of the user, in an example, the method includes detecting the brain wave information of the user using a built-in brain wave sensor in the sensor device.

To detect the brain wave information of the user using the built-in brain wave sensor in the sensor device, the method includes determining a contact position where the user is in touch with the sensor device, and detecting the brain wave information of the user using the built-in brain wave sensor that is selected from a plurality of built-in brain wave sensors in the senor device, and is the closest to the contact position.

In an embodiment, to acquire the brain wave information of the user, the method includes receiving the acquired brain wave information of the user transmitted by a brain wave detector.

To acquire the brain wave information of the user, in an example, the method includes acquiring at least one of a frequency, an amplitude and a waveform of brain wave parameters of the user, and determining a brain wave type corresponding to the acquired brain wave parameter as the brain wave information of the user. To determine the brain wave type corresponding to the acquired brain wave parameter as the brain wave information of the user, the method includes retrieving the brain wave type corresponding to the acquired brain wave parameter from a first preset relationship table which records corresponding relationships between different brain wave parameters and brain wave types.

To acquire the brain wave information of the user, in another example, the method includes acquiring at least one of a frequency, an amplitude and a waveform of brain wave parameters of the user, acquiring at least one of an age, a gender and a health state of physiological parameters of the user, and determining a brain wave type corresponding to the acquired brain wave parameter and the acquired physiological parameter as the brain wave information of the user. To determine the brain wave type corresponding to the acquired brain wave parameter and the acquired physiological parameter as the brain wave information of the user, the method includes retrieving the brain wave type corresponding to the acquired brain wave parameter and the acquired physiological parameter from a second preset relationship table which records corresponding relationships among different brain wave parameters, physiological parameters and brain wave types.

To control the electronic device based on the brain wave information, in an example, the method includes when the brain wave information has a type identification of a β wave or an α wave, controlling the electronic device to continue a previous operation of preset data. In another example, the method includes when the brain wave information has the type identification of a δ wave, controlling the electronic device to stop the previous operation of preset data. In another example, the method includes when the brain wave information has the type identification of any of a θ wave, a hump wave, a K-complex wave and a sleep spindle wave, outputting prompt information for changing the preset data. In another example, the method includes when the brain wave information has the type identification of any of a θ wave, a hump wave, a K-complex wave and a sleep spindle wave, reducing a sound volume.

To control the electronic device based on the brain wave information, in an example, the method includes generating a control command based on the brain wave information and sending the control command to a media play device to trigger the media play device to execute a play response to the brain wave information. In an example, when the brain wave information has a type identification of a δ wave, the control command is used to control the media play device to stop playing preset data. In another example, when the brain wave information has the type identification of any of a θ wave, a hump wave, a K-complex wave and a sleep spindle wave, the control command is used to control the media play device to output prompt information for changing the preset data. In another example, when the brain wave information has the type identification of any of a θ wave, a hump wave, a K-complex wave and a sleep spindle wave, the control command is used to control the media play device to reduce a play sound volume for playing the preset data.

Aspects of the disclosure provide a terminal device that includes a processor and a memory storing instructions executable by the processor. The processor is configured to acquire brain wave information of a user, and control an electronic device associated with the user based on the brain wave information.

According to an aspect of the disclosure, the processor is configured to receive touch attributes of an object that is in touch with a sensor device, determine whether at least one of the touch attributes of the object meets a preset condition, determine that the object in touch with the sensor device is the user when the at least one of the touch attributes meets the preset condition, and acquire the brain wave information of the user. In an example, the processor is configured to when a shape of the object detected by a built-in area sensor in the sensor device matches with a preset shape, determine that the detected shape meets the corresponding preset condition. In another example, the processor is configured to when a temperature of the object detected by a built-in temperature sensor in the sensor device matches with a preset temperature, determine that the detected temperature meets the corresponding preset condition. In another example, the processor is configured to when a pressure of the object is detected by a built-in pressure sensor, an area of the object is detected by the built-in area sensor, and a ratio of the pressure to the area matches with a preset density, determine that the detected pressure and area meet the corresponding preset condition.

In an embodiment, the processor is also configured to determine a contact position where the user is in touch with a sensor device, and detect the brain wave information of the user using a built-in brain wave sensor that is selected from a plurality of built-in brain wave sensors and is closest to the contact position in the sensor device.

According to an aspect of the disclosure, the processor is also configured to acquire at least one of a frequency, an amplitude and a waveform of brain wave parameters of the user and determine a brain wave type corresponding to the acquired brain wave parameter as the brain wave information of the user.

In an example, the processor is configured to acquire at least one of a frequency, an amplitude and a waveform of brain wave parameters of the user, acquire at least one of an age, a gender and a health state of physiological parameters of the user, and determine a brain wave type corresponding to the acquired brain wave parameter and the acquired physiological parameter as the brain wave information of the user.

In an embodiment, the processor is also configured to generate a control command corresponding with the brain wave information, and send the control command to a media play device to trigger the media play device to execute a play response to the brain wave information. In an example, when the brain wave information has a type identification of a δ wave, the control command is used to control the media play device to stop playing preset data. In another example, when the brain wave information has the type identification of any of a θ wave, a hump wave, a K-complex wave and a sleep spindle wave, the control command is used to control the media play device to output prompt information for changing the preset data. In another example, when the brain wave information has the type identification of any of a θ wave, a hump wave, a K-complex wave and a sleep spindle wave, the control command is used to control the media play device to reduce a play sound volume for playing the preset data.

It should be understood that both the foregoing general description and the following detailed description are exemplary and explanatory only and are not restrictive of the invention.

BRIEF DESCRIPTION OF THE DRAWINGS

The accompanying drawings, incorporated in and constitute a part of this specification, illustrate embodiments consistent with the invention and, together with the description, serve to explain the principles of the invention.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise presented. The embodiments set forth in the following description of exemplary embodiments do not represent all embodiments consistent with the invention. Instead, they are merely examples of apparatuses and methods consistent with aspects related to the invention as recited in the appended claims.

The terms used in this disclosure are only intended to describe the specific embodiments rather than to limit this disclosure. The terms such as "a/an", "the" and "said" in single forms used in this disclosure and the appended claims are also intended to include plural forms, unless clearly specified otherwise in the context. It should be noted that, the term "and/or" used herein includes any or all combinations of one or more related listed items.

It should be noted that although terms such as "first", "second" and "third" are used to describe various information, such information shall not be limited to these terms. These terms are only used to distinguish information of the same type. For example, when not departing from the scope of this disclosure, first information may also be named as second information, and vice versa. Depending on the context, the word "if" used herein may be interpreted as "when" or "determining that . . . in response to".

Figure 1:
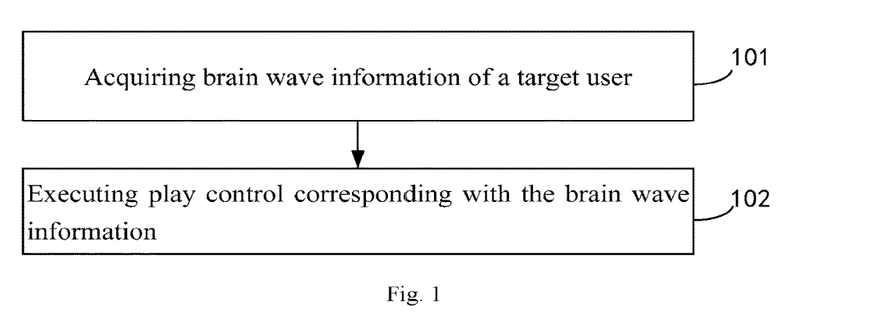
FIG. 1 is a flow chart showing a play control method according to an exemplary embodiment of this disclosure.

As shown in FIG. 1, FIG. 1 is a flow chart showing a play control method according to an exemplary embodiment of this disclosure. The method may be used in a terminal and comprises steps 101-102 as below:

Step 101: acquiring brain wave information of a target user; and

Step 102: executing play control corresponding with the brain wave information.

When this embodiment of this disclosure is applied, by acquiring brain wave information of a target user and executing play control corresponding with the brain wave information, the state of the target user can be reflected through the brain wave information; accordingly, effective control of the user's needs can be realized through the brain wave information without any triggering operation by the user, thereby enhancing the user experience and improving the intelligence level of play devices.

The embodiments of this disclosure may be executed by a play device used for playing at least one type of information including characters, graphics, images, audio, video, animation and the like. The play device includes computers, tablet computers, televisions, mobile phones, personal stereos, hand-held readers and the like. The embodiments of this disclosure may be executed by a control device that executes play control to the play device. The play device may have a play control function or both a play control function and a brain wave information detection function. The control device may have a brain wave information detection function.

Regarding step 101, the brain wave information may include at least one brain wave parameter from the frequency, the amplitude and the waveform of the brain wave, or may include the type identification of various brain wave types divided based on the parameters, such as the frequency, the amplitude and the waveform of the brain wave. The target user may be a person contacting a play device, a control device or a brain wave detection device. In other optional solutions, the target user may be other objects having brain waves and contacting a play device, a control device or a brain wave collection device, or may be other objects having brain waves and spaced from the play device, the control device or the brain wave collection device a preset distance.

In the embodiments of this disclosure, acquiring the brain wave information of the target user may comprise detecting the brain wave information of the target user using an in-built brain wave sensor. The brain wave sensor is built in the executing device of the embodiments of this disclosure. The detected brain wave information may be brain wave parameters such as the frequency, the amplitude and the waveform of the brain wave, or the type identification of various brain wave types divided based on the brain wave information parameters, such as the frequency, the amplitude and the waveform of the brain wave.

In the embodiments of this disclosure, acquiring the brain wave information of the target user may comprise receiving the brain wave information of the target user transmitted by a brain wave detector. The brain wave detector and the executing device are separately provided in the embodiments of this disclosure. The transmitted brain wave information may be brain wave parameters such as the frequency, the amplitude and the waveform of the brain wave, or the type identification of various brain wave types divided based on the brain wave information parameters, such as the frequency, the amplitude and the waveform of the brain wave.

Before acquiring the brain wave information of the target user, detection may be performed to determine whether the object contacting the target device is the target user. When the object is the target user, the brain wave information of the target user is acquired. The target device may be the play device or the control device that executes the embodiments of this disclosure, a sleep device for playing sleep music, a remote control pillow or mattress or hat having a control function. The target device may be separately provided from the play device or the control device that executes the embodiments of this disclosure, and may be a preset device contacted by the user, such as a mattress, a pillow, a headrest or a hat. The target device may be the brain wave detector separately provided from the executing device of the embodiments of this disclosure.

In the embodiments of this disclosure, detecting whether the object contacting a target device is the target user comprises: determining if at least one parameter of the contact parameters representing the contact of the object and the target device meets a corresponding preset condition; and determining that the object contacting the target device is the target user if at least one parameter of the contact parameters meets the corresponding preset condition.

Determining whether at least one parameter of the contact parameters representing the contact of the object and the target device meets the corresponding preset condition comprises one or more the following modes:

Mode 1: if the contact parameter comprises a shape, and the shape of the object detected by an in-built area sensor matches with a preset shape, determining that the detected shape meets the corresponding preset condition.

The area sensor may be built in the play device or the control device that executes the embodiments of this disclosure, or in the target device independent from the play device or the control device, or in other preset device. For example, the area sensor may be built in a mattress. The target device may be a pillow. An area of the object contacting the mattress may be acquired through the area sensor. The shape of the object may be acquired through the area. If the shape matches that of a human, it is determined that the detected shape meets the corresponding preset condition, and that the object contacting the target device is a human.

Mode 2: if the contact parameter comprises a temperature, and the temperature of the object detected by an in-built temperature sensor matches with a preset temperature, determining that the detected temperature meets the corresponding preset condition.

The temperature sensor may be built in the play device or the control device that executes the embodiments of this disclosure, or in the target device independent from the play device or the control device, or in other preset device. For example, the temperature sensor may be built in a mattress. The target device may be a pillow. If the temperature acquired by the temperature sensor falls into the scope of a human's body temperature, it is determined that the detected temperature meets the corresponding preset condition, and that the object contacting the target device is a human.

Mode 3: if the contact parameter comprises a pressure and an area, and a ratio of the pressure of the object detected by an in-built pressure sensor to the area of the object detected by an in-built area sensor matches with a preset density, determining that the detected pressure and area meet the corresponding preset condition.

The area sensor and the pressure sensor may be built in the play device or the control device that executes the embodiments of this disclosure, or in the target device independent from the play device or the control device, or in other preset device.

Detecting the brain wave information of the target user using an in-built brain wave sensor may comprise: determining a contact position where the target user contacts the target device; and detecting the brain wave information of the target user using an in-built brain wave sensor closest to the contact position. The contact position can be determined by a pressure-sensitive sensor built in the target device. Brain wave information can be detected more accurately by the brain wave sensor closest to the contact position, so that the accuracy and effectiveness of play control can be improved.

Regarding step 102, corresponding relations between various brain wave information and various play control can be preset, and play control corresponding with the brain wave information can be performed based on the preset corresponding relations. The play control may include ordinary control of characters, graphics, images, audio, video, animation and the like played by a play device, such as continuing, switching, pausing, reducing the sound volume and the like. The corresponding relations between various brain wave information and various play control may include corresponding relations between at least one brain wave parameter from the frequency, the amplitude, the waveform, the type identification and the like and various play control.

Brain waves may be divided into four types: a $\delta$ wave, a $\theta$ wave, an $\alpha$ wave and a $\beta$ wave. The corresponding brain wave information may include at least one of the type identification of a $\delta$ wave, the type identification of a $\theta$ wave, the type identification of an $\alpha$ wave and the type identification of a $\beta$ wave.

An $\alpha$ wave may appear when a healthy adult is calm or feels happy. Its frequency range is 8-13 Hz and its amplitude range is 20-100 $\mu$V. It is mainly distributed in the parietal occipital region, and is usually in the shape of a sine wave. It also changes depending on the brain development level or the age. The number of $\alpha$ waves of children gradually increases as their brains mature, and the frequency of the $\alpha$ wave also increases until it becomes steady in the adulthood. The frequency of the $\alpha$ wave slows down in old age.

A $\beta$ wave may appear when a nervous or exciting feeling appears. Its frequency range is 14-30 Hz and its amplitude range is 5-20 $\mu$V. It may be distributed across the whole brain, and is mainly distributed in the anterior hemisphere and the temporal region. It is related with gender, psychological state, personal character and age. A $\beta$ wave appears more often in women than men, and more often in old people than adults. When humans have unstable mood, are applied with tranquilizers or hypnotics, $\beta$ waves will increase and their amplitude will also increase.

A $\theta$ wave appears more often when a human is tired or has fallen asleep. Its frequency range is 4-7 Hz and its amplitude range is 100-150 $\mu$V. It is a main component of an electroencephalogram of young people aged between 10 and 17. It is mainly distributed in the upper apex and the temporal region. Its number gradually decreases, its frequency gradually increases and its amplitude gradually decreases from children to adults. Few $\theta$ waves will appear in the electroencephalogram of an adult. When an adult feels depressed, disappointed or frustrated, about 20 seconds of $\theta$ waves may appear. A $\theta$ wave is common for old people and sick people.

A $\delta$ wave may appear when an adult is totally exhausted or sleepy or has severe encephalosis or when a child is immature in intelligence. Its frequency range is 1-3 Hz and its amplitude range is 20-200 $\mu$V. A $\delta$ wave may appear in the brain record of an animal that has gone through a subcortical transection surgery. A $\delta$ wave can only appear in the cortex, and is not controlled by the nerves of lower parts of the brain.

In addition, there may be normal brain waves having special waveforms, such as hump waves, $\sigma$ rhythm waves, $\lambda$ waves, k-complex waves, $\mu$ rhythm waves and the like.

A $\mu$ rhythm wave is a comb rhythm having a frequency of 8-12 Hz. It may be distributed in the central region. When $\mu$ a rhythm waves appear in the central regions of the both sides, they may be asynchronous and asymmetrical. When eyes are open, $\mu$ rhythm waves do not disappear. When a fist is made at the opposite side or metal activities are suppressed due to stimulus of feelings, $\mu$ rhythm waves may disappear temporarily; this case may occur to a healthy human, a human having a nerve illness or brain trauma etc., but the implications are unclear.

A vertex sharp transient wave or a hump wave is a negative vertex sharp wave simultaneously appearing in the apex and central regions in a preliminary stage of light sleep, with the apex region more prominent. Its frequency range is 3-5 Hz and its amplitude range is 100-300 μV. When a pair of hump waves appear, they are also called "Double Hump Waves".

A sleep spindle wave is also called a σ rhythm wave. The frequency range of a σ rhythm wave of an adult may be 12-14 Hz, and the frequency range of a σ rhythm wave of a child may be 10-12 Hz. It is mainly distributed in the apex/central region. For children, σ rhythm waves may be asynchronous for the left and right sides. For people aged 60 or older, σ rhythm waves remarkably reduce or disappear. A σ rhythm wave is a main indicator of brain wave in the light sleep period.

A K-complex wave is a complex wave composed of a vertex sharp transient wave and a σ rhythm wave. It may appear automatically in the light sleep period or due to triggering of external feeling stimulus, in particular sound stimulus. Usually, it appears symmetrically on both sides. A σ rhythm wave is an awakening reaction in normal sleep.

As known from the above brain waves, in the embodiments of this disclosure, acquiring the brain wave information of the target user may comprise: acquiring at least one brain wave parameter of the frequency, the amplitude and the waveform from the target user; and determining the brain wave type corresponding with the acquired brain wave parameter as the brain wave information of the target user. The brain wave information of the target user can be acquired quickly and accurately through the parameters such as a frequency, an amplitude and a waveform, thereby improving the play control efficiency.

Determining the brain wave type corresponding with the acquired brain wave parameter as the brain wave information of the target user may comprise: retrieving the brain wave type corresponding with the acquired brain wave parameter from a first preset relationship table which records corresponding relationships between different brain wave parameters and brain wave types.

In the embodiments of this disclosure, acquiring the brain wave information of the target user may comprise: acquiring at least one brain wave parameter of the frequency, the amplitude and the waveform from the target user; acquiring at least one physiological parameter of the age, the gender and the health state from the target user; and determining the brain wave type corresponding with the acquired brain wave parameter and the acquired physiological parameter as the brain wave information of the target user. The brain wave information of the target user can be acquired quickly and accurately through the parameters such as a frequency, an amplitude, a waveform, an age, gender and health state, thereby improving the play control efficiency.

Determining a brain wave type corresponding with an acquired brain wave parameter and an acquired physiological parameter as the brain wave information of the target user may comprise: retrieving a brain wave type corresponding with the acquired brain wave parameter and the acquired physiological parameter from a second preset relationship table which records corresponding relationships among different brain wave parameters, physiological parameters and brain wave types.

For example, image information of the target user may be acquired by a camera. Gender and age of the target user may be acquired by processing the acquired image information. Medical record corresponding with the image information of the target user may be acquired from a medical record server. The health state of the target user may be acquired by performing information extraction to the medical record.

The play control corresponding with the brain wave information executed in the embodiments of this disclosure is directed to the brain activities of the user, and can effectively reflect the implementation needs of the user. Effective control of the user's needs can be realized through the brain wave information without any triggering operation by the user, thereby enhancing the user experience and improving the intelligence level of play devices.

Figure 2:
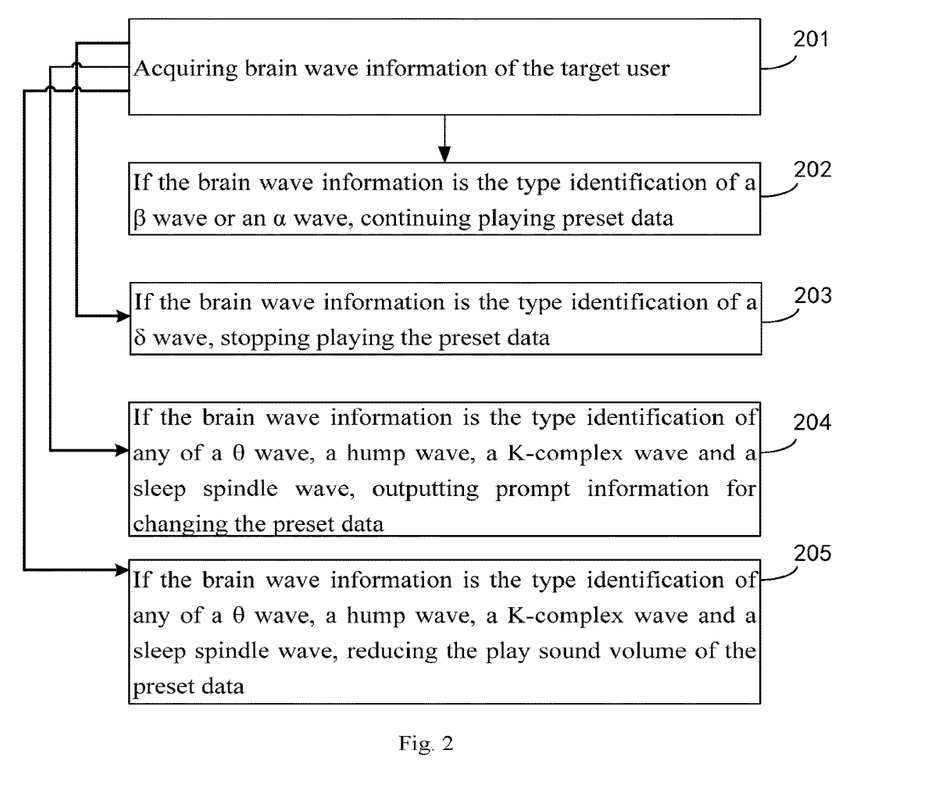
FIG. 2 is a flow chart showing a play control method according to another exemplary embodiment of this disclosure.

As shown in FIG. 2, FIG. 2 is a flow chart showing a play control method according to another exemplary embodiment of this disclosure. The method comprises steps 201-205:

Step 201: acquiring the brain wave information of the target user;

Step 202: if the brain wave information is the type identification of a β wave or an α wave, continuing playing preset data;

Step 203: if the brain wave information is the type identification of a δ wave, stopping playing the preset data;

Step 204: if the brain wave information is the type identification of any of a θ wave, a hump wave, a K-complex wave and a sleep spindle wave, outputting prompt information for changing the preset data; or Step 205: if the brain wave information is the type identification of any of a θ wave, a hump wave, a K-complex wave and a sleep spindle wave, reducing the play sound volume of the preset data.

In the embodiments of this disclosure, by executing different play control for different types of brain waves, this disclosure can improve the flexibility of play control.

The preset data may be at least one of characters, graphics, images, audio, video, animation and the like. For example, the preset data may be audio and video data corresponding with movie and TV programs. The type identification may be a frequency range, an amplitude range, a waveform name or a wave name of various brain waves.

In the embodiments of this disclosure, outputting prompt information for changing the preset data may be performed by the following one or more modes:

Mode 1: playing a voice prompt for changing the preset data, wherein the voice prompt may include voice identification of the data to be played;

Mode 2: popping an information block including other preset data; and

Mode 3: top displaying a play menu including various play data.

In other embodiments of this disclosure, play control different from that of the embodiments of this disclosure may be performed according to different types of brain waves. For example, when the brain wave is a δ wave, a clock alarm may be played to prompt the user; when the brain wave is any of a θ wave, a hump wave, a K-complex wave and a sleep spindle wave, play of the preset data is stopped and sleep music is played.

Figure 3:
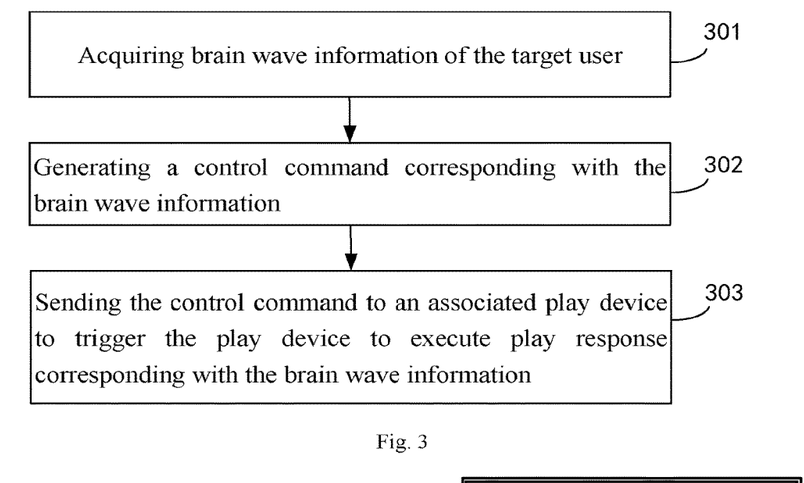
FIG. 3 is a flow chart showing a play control method according to another exemplary embodiment of this disclosure.

As shown in FIG. 3, FIG. 3 is a flow chart showing a play control method according to another exemplary embodiment of this disclosure. The method comprises steps 301-303:

Step 301: acquiring the brain wave information of the target user;

Step 302: generating a control command corresponding with the brain wave information; and Step 303: sending the control command to an associated play device to trigger the play device to execute play response corresponding with the brain wave information.

In the embodiments of this disclosure, by generating a control command corresponding with the brain wave information and sending the control command to an associated play device to trigger the play device to execute play response corresponding with the brain wave information, this disclosure can execute play control for different play devices.

The associated play device may be a preset device to be controlled, or for example, a play device within a preset distance relative to the target user or the control device of the embodiments of this disclosure.

If the brain wave information is the type identification of a δ wave, the control command is configured to stop playing preset data.

If the brain wave information is the type identification of any of a θ wave, a hump wave, a K-complex wave and a sleep spindle wave, the control command is configured to output prompt information for changing the preset data; or if the brain wave information is the type identification of any of a θ wave, a hump wave, a K-complex wave and a sleep spindle wave, the control command is configured to reduce the play sound volume of the preset data.

In other embodiments of this disclosure, control commands corresponding with the brain wave information and different from that in the embodiments of this disclosure may be generated. For example, if the brain wave information is the type identification of a δ wave, the control command is configured to play a clock alarm; if the brain wave information is the type identification of any of a θ wave, a hump wave, a K-complex wave and a sleep spindle wave, the control command is configured to stop playing the preset data and play sleep music.

Figure 4:
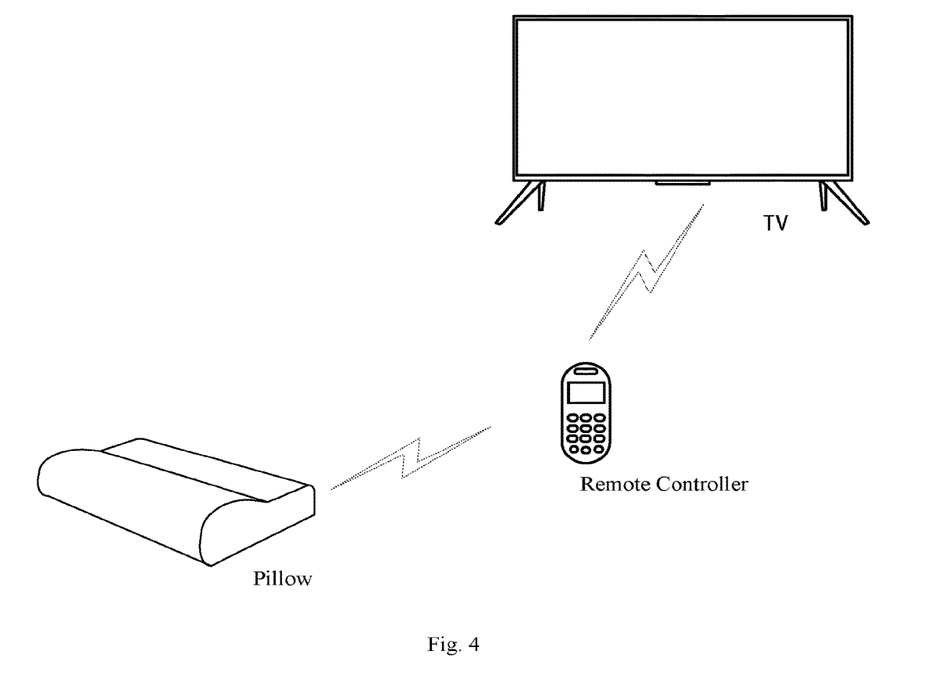
FIG. 4 is a schematic application scene of a play control method according to an exemplary embodiment of this disclosure.

As shown in FIG. 4, FIG. 4 is a schematic application scene of a play control method according to an exemplary embodiment of this disclosure. The scene shown in FIG. 4 includes a pillow as a brain wave detector, a remote controller as a control device and a TV as a play device. The pillow and the remote controller are wirelessly connected, and can transmit and exchange information therebetween on the basis of wireless connection. The remote controller and the TV are wirelessly connected, and can transmit and exchange information therebetween on the basis of wireless connection. It should be understood that the brain wave detector is only embodied as a pillow in the embodiments of this disclosure; the control device is only embodied as a remote controller in the embodiments of this disclosure; and the play device is only embodied as a TV in the embodiments of this disclosure. The brain wave detector in the present embodiment may be a headrest, a hat or other articles; the play device may be a personal computer PC, a DVD or other digital broadcast terminals; and the control device may be a smart cell phone or other smart terminals.

In the application scene shown in FIG. 4, the pillow shown in FIG. 4 detects the brain wave information of the target user contacting the pillow, and sends the detected brain wave information to the remote controller shown in FIG. 4. The remote controller generates a control command corresponding with the brain wave information, and sends the same to the TV shown in FIG. 4, which executes play response corresponding with the brain wave information.

For example, when the brain wave information is the frequency of a brain wave, the remote controller can identify the type identification of the brain wave on the basis of the frequency thereof, generates a control command corresponding with the type identification and sends the same to the TV shown in FIG. 4, taking the control command as the control command corresponding with the frequency of the brain wave.

Figure 5:
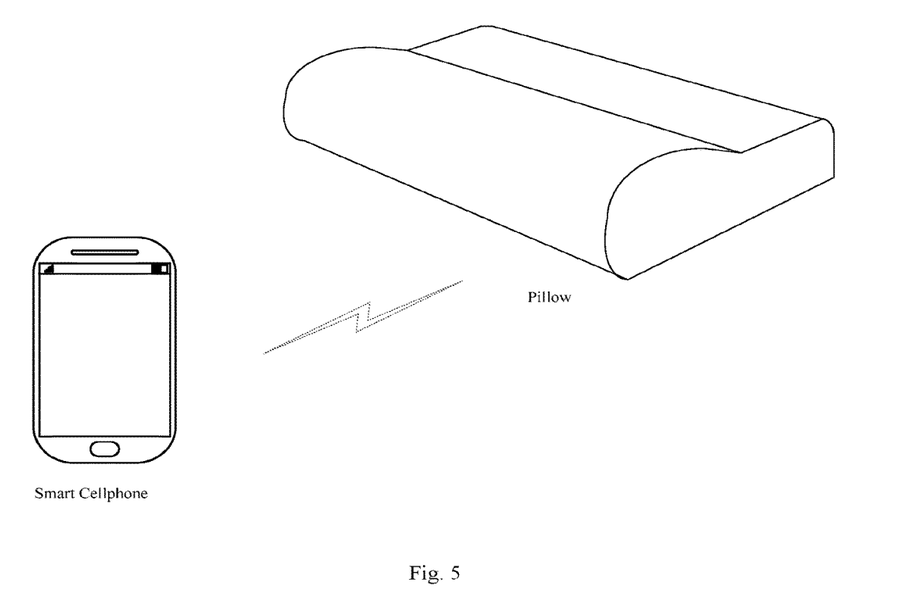
FIG. 5 is a schematic application scene of a play control method according to another exemplary embodiment of this disclosure.

As shown in FIG. 5, FIG. 5 is a schematic application scene of a play control method according to an exemplary embodiment of this disclosure. The scene shown in FIG. 5 includes a pillow as a brain wave detector and a smart cellphone as a play device. The pillow and the smart cellphone are wirelessly connected, and can transmit and exchange information therebetween on the basis of wireless connection. It should be understood that the brain wave detector is only embodied as a pillow in the embodiments of this disclosure; and the play device is only embodied as a smart cellphone in the embodiments of this disclosure. The brain wave detector in the present embodiment may be a headrest, a hat or other articles; and the play device may be a tablet computer or other smart terminals.

In the application scene shown in FIG. 5, the pillow shown in FIG. 5 detects the brain wave information of the target user contacting the pillow, and sends the detected brain wave information to the smart cellphone shown in FIG. 5. The smart cellphone executes play control corresponding with the brain wave information based on the same.

For example, when the brain wave information is the frequency of a brain wave, the smart cellphone can identify the type identification of the brain wave on the basis of the frequency thereof, taking the play control corresponding with the type identification as the play control corresponding with the frequency of the brain wave.

In other application scenes of this disclosure, the pillow shown in FIG. 5 detects the brain wave information of the target user contacting the pillow, may generate a control command corresponding with the brain wave information of the same basis, and may sends the control command to the play device. The play device performs play control corresponding with the brain wave information in response to the control command.

For example, when the brain wave information is the frequency of a brain wave, the pillow can identify the type identification of the brain wave on the basis of the frequency thereof, generates a control command corresponding with the type identification and sends the same to the play device, taking the generated control command as the control command corresponding with the frequency of the brain wave.

Corresponding with the embodiments of the play control method described above, this disclosure also provides embodiments of a play control apparatus and a corresponding terminal.

Figure 6:
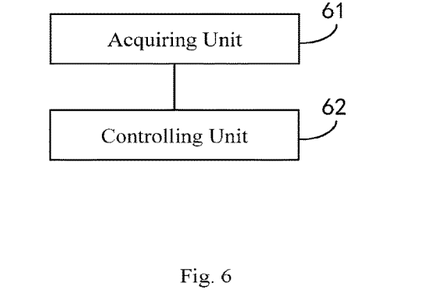
FIG. 6 is a block diagram showing a play control apparatus according to an exemplary embodiment of this disclosure.

As shown in FIG. 6, FIG. 6 is a block diagram showing a play control apparatus according to an exemplary embodiment of this disclosure. The play control apparatus comprises an acquiring unit 61 and a controlling unit 62.

The acquiring unit 61 81 is configured to acquire brain wave information of a target user.

The controlling unit 62 is configured to execute play control corresponding with the brain wave information.

When this embodiment of this disclosure is applied, by acquiring brain wave information of a target user and executing play control corresponding with the brain wave information, the state of the target user can be reflected through the brain wave information; accordingly, effective control of the user's needs can be realized through the brain wave information without any triggering operation by the user, thereby enhancing the user experience and improving the intelligence level of play devices.

Figure 7:
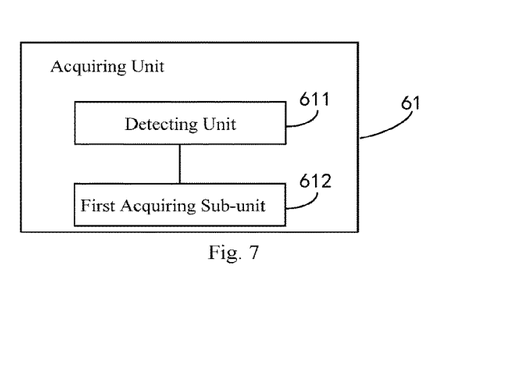
FIG. 7 is a block diagram showing a play control apparatus according to another exemplary embodiment of this disclosure.

As shown in FIG. 7, FIG. 7 is a block diagram showing a play control apparatus according to another exemplary embodiment of this disclosure. The acquiring unit 61 may include a detecting unit 611 and a first acquiring sub-unit 612 based on the embodiment shown in FIG. 6.

The detecting unit 611 is configured to detect if the object contacting a target device is the target user.

The first acquiring sub-unit 612 is configured to acquire the brain wave information of the target user if the object is the target user.

When this embodiment of this disclosure is applied, by detecting whether the object contacting a target device is the target user and acquiring the brain wave information of the target user, this disclosure can prevent from acquiring information of an invalid object, thereby increasing the play control efficiency.

Figure 8:
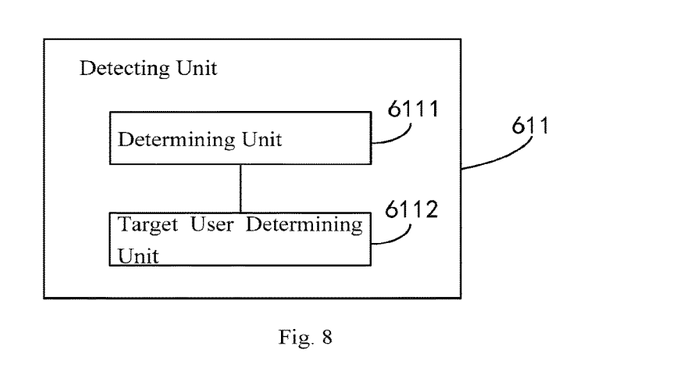
FIG. 8 is a block diagram showing a play control apparatus according to another exemplary embodiment of this disclosure.

As shown in FIG. 8, FIG. 8 is a block diagram showing a play control apparatus according to another exemplary embodiment of this disclosure. The detecting unit 611 may include a determining unit 6111 and a target user determining unit 6112 based on the embodiment shown in FIG. 7.

The determining unit 6111 is configured to determine if at least one parameter of the contact parameters representing the contact of the object and the target device meets a corresponding preset condition.

The target user determining unit 6112 is configured to determine that the object contacting the target device is the target user if at least one parameter of the contact parameters meets the corresponding preset condition.

When this embodiment of this disclosure is applied, by determining the object contacting the target device and the contact parameters representing the contact of the object and the target device, the object can be determined as the target user quickly, so this disclosure can increase the play control efficiency.

Figure 9:
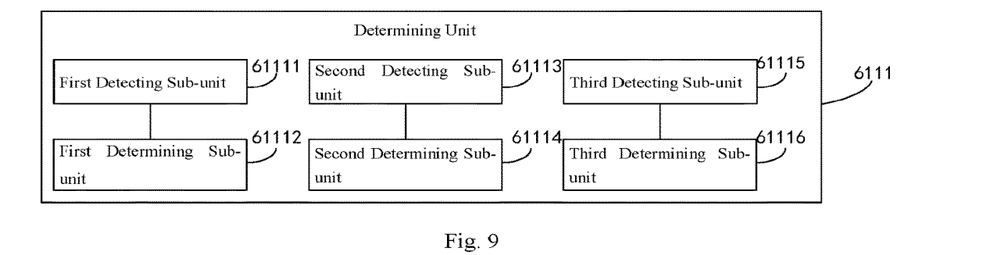
FIG. 9 is a block diagram showing a play control apparatus according to another exemplary embodiment of this disclosure.

As shown in FIG. 9, FIG. 9 is a block diagram showing a play control apparatus according to another exemplary embodiment of this disclosure. The determining unit 6111 may include at least one pair of a detecting sub-unit and a determining sub-unit selected from a first detecting sub-unit 61111, a first determining sub-unit 61112, a second detecting sub-unit 61113, a second determining sub-unit 61114, a third detecting sub-unit 61115 and a third determining sub-unit 61116 based on the embodiment shown in FIG. 8. To facilitate illustration, the above six sub-units are shown in FIG. 9.

The first detecting sub-unit 61111 is configured to acquire the shape of the object using an in-built area sensor if the contact parameter comprises the shape.

The first determining sub-unit 61112 is configured to determine that the detected shape meets the corresponding preset condition if the shape matches with a preset shape.

The second detecting sub-unit 61113 is configured to acquire the temperature of the object using an in-built temperature sensor if the contact parameter comprises the temperature.

The second determining sub-unit 61114 is configured to determine that the detected temperature meets the corresponding preset condition if the temperature matches with preset temperature information.

The third detecting sub-unit 61115 is configured to acquire the area and the pressure of the object using an in-built area sensor and an in-built pressure sensor if the contact parameter comprises the pressure and area.

The third determining sub-unit 61116 is configured to determine that the detected area and pressure meet the corresponding preset condition if a ratio of the pressure to the area matches with a preset density.

When this embodiment of this disclosure is applied, by determining the object contacting the target device as the target user more accurately and quickly through an in-built area sensor, an in-built pressure or temperature sensor, this disclosure can increase the play control efficiency.

Figure 10:
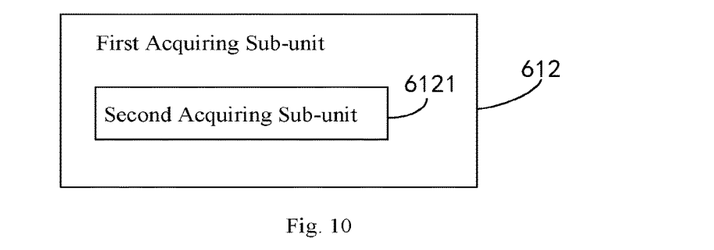
FIG. 10 is a block diagram showing a play control apparatus according to another exemplary embodiment of this disclosure.

As shown in FIG. 10, FIG. 10 is a block diagram showing a play control apparatus according to another exemplary embodiment of this disclosure. The first acquiring sub-unit 612 may include a second acquiring sub-unit 6121 based on the embodiment shown in FIG. 7.

The second acquiring sub-unit 6121 is configured to detect the brain wave information of the target user using an in-built brain wave sensor.

When this embodiment of this disclosure is applied, by detecting the brain wave information of the target user using an in-built brain wave sensor, the brain wave information of the target user can be acquired accurately and quickly, so this disclosure can increase the play control accuracy and effectiveness.

Figure 11:
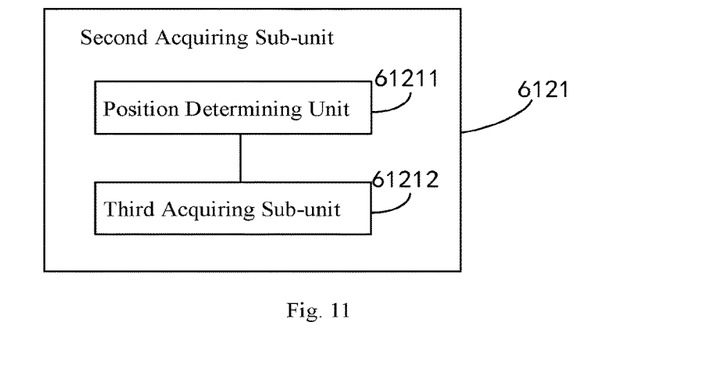
FIG. 11 is a block diagram showing a play control apparatus according to another exemplary embodiment of this disclosure.

As shown in FIG. 11, FIG. 11 is a block diagram showing a play control apparatus according to another exemplary embodiment of this disclosure. The second acquiring sub-unit 6121 may include a position determining unit 61211 and a third acquiring sub-unit 61212 based on the embodiment shown in FIG. 10.

The position determining unit 61211 is configured to determine a contact position where the target user contacts the target device.

The third acquiring sub-unit 61212 is configured to detect the brain wave information of the target user using an in-built brain wave sensor closest to the contact position.

When this embodiment of this disclosure is applied, after determining the contact position where the target user contacts the target device, the brain wave information of the target user can be acquired accurately using an in-built brain wave sensor closest to the contact position, so this disclosure can increase the play control accuracy and effectiveness.

Figure 12:
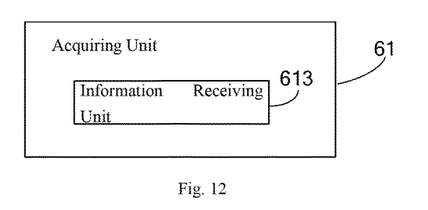
FIG. 12 is a block diagram showing a play control apparatus according to another exemplary embodiment of this disclosure.

As shown in FIG. 12, FIG. 12 is a block diagram showing a play control apparatus according to another exemplary embodiment of this disclosure. The acquiring unit 61 may include an information receiving unit 613 based on the embodiment shown in FIG. 6.

The information receiving unit 613 is configured to receive the acquiring brain wave information of the target user transmitted by a brain wave detector.

When this embodiment of this disclosure is applied, by receiving the brain wave information of the target user transmitted by a brain wave detector at a terminal, the terminal of this disclosure does not need to directly detect the brain wave information of the target user, so that the terminal can receive the brain wave information of different target users, allowing the terminal to execute display control to different target users.

Figure 13:
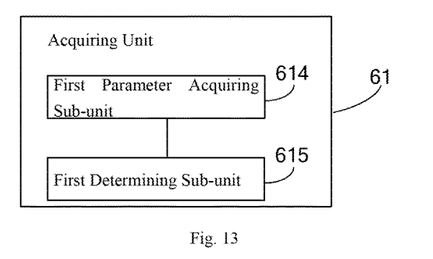
FIG. 13 is a block diagram showing a play control apparatus according to another exemplary embodiment of this disclosure.

As shown in FIG. 13 FIG. 13 is a block diagram showing a play control apparatus according to another exemplary embodiment of this disclosure. The acquiring unit 61 may include a first parameter acquiring sub-unit 614 and a first determining sub-unit 615 based on the embodiment shown in FIG. 6.

The first parameter acquiring sub-unit 614 is configured to acquire at least one brain wave parameter of the frequency, the amplitude and the waveform from the target user.

The first determining sub-unit 615 is configured to determine the brain wave type corresponding with the acquired brain wave parameter as the brain wave information of the target user.

When this embodiment of this disclosure is applied, by acquiring at least one brain wave parameter the frequency, the amplitude and the waveform from the target user, and determining the brain wave type corresponding with the acquired brain wave parameter as the brain wave information of the target user, the brain wave information of the target user can be identified quickly and accurately, so this disclosure can increase the play control efficiency.

Figure 14:
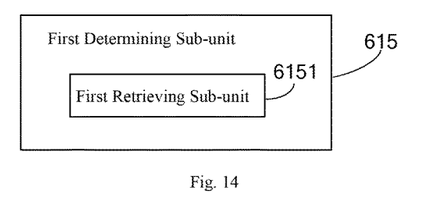
FIG. 14 is a block diagram showing a play control apparatus according to another exemplary embodiment of this disclosure.

As shown in FIG. 14, FIG. 14 is a block diagram showing a play control apparatus according to another exemplary embodiment of this disclosure. The first determining sub-unit 615 may include a first retrieving sub-unit 6151 based on the embodiment shown in FIG. 13.

The first retrieving sub-unit 6151 is configured to retrieve the brain wave type corresponding with the acquired brain wave parameter from a first preset relationship table which records corresponding relationships between different brain wave parameters and brain wave types.

When this embodiment of this disclosure is applied, the type of the brain wave can be determined quickly through a first preset relationship table which records corresponding relationships between different brain wave parameters and brain wave types, so this disclosure can increase the play control efficiency.

Figure 15:
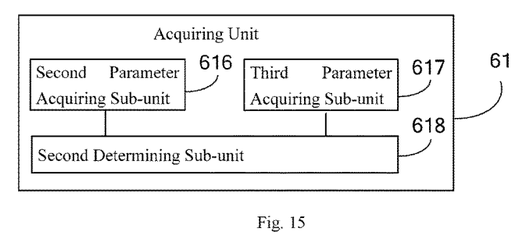
FIG. 15 is a block diagram showing a play control apparatus according to another exemplary embodiment of this disclosure.

As shown in FIG. 15 FIG. 15 is a block diagram showing a play control apparatus according to another exemplary embodiment of this disclosure. The acquiring unit 61 may include a second parameter acquiring sub-unit 616, a third parameter acquiring sub-unit 617 and a second determining sub-unit 618 based on the embodiment shown in FIG. 6.

The second parameter acquiring sub-unit 616 is configured to acquire at least one brain wave parameter of the frequency, the amplitude and the waveform from the target user.

The third parameter acquiring sub-unit 617 is configured to acquire at least one physiological parameter of the age, the gender and the health state from the target user.

The second determining sub-unit 618 is configured to determine the brain wave type corresponding with the acquired brain wave parameter and the acquired physiological parameter as the brain wave information of the target user.

When this embodiment of this disclosure is applied, by acquiring at least one brain wave parameter of the frequency, the amplitude and the waveform from the target user, acquiring at least one physiological parameter of the age, the gender and the health state from the target user, and determining the brain wave type corresponding with the acquired brain wave parameter and t acquired physiological parameter as the brain wave information of the target user, the brain wave information of the target user can be identified quickly and accurately, so this disclosure can increase the play control efficiency.

Figure 16:
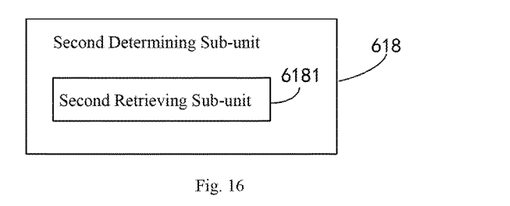
FIG. 16 is a block diagram showing a play control apparatus according to another exemplary embodiment of this disclosure.

As shown in FIG. 16, FIG. 16 is a block diagram showing a play control apparatus according to another exemplary embodiment of this disclosure. The second determining sub-unit 618 may include a second retrieving sub-unit 6181 based on the embodiment shown in FIG. 15.

The second retrieving sub-unit 6181 is configured to retrieve a brain wave type corresponding with the acquired brain wave parameter and the acquired physiological parameter from a second preset relationship table which records corresponding relationships among different brain wave parameters, physiological parameters and brain wave types.

When this embodiment of this disclosure is applied, the type of the brain wave can be determined quickly through a relationship table which records corresponding relationships among different brain wave parameters, physiological parameters and brain wave types, so this disclosure can increase the play control efficiency.

Figure 17:
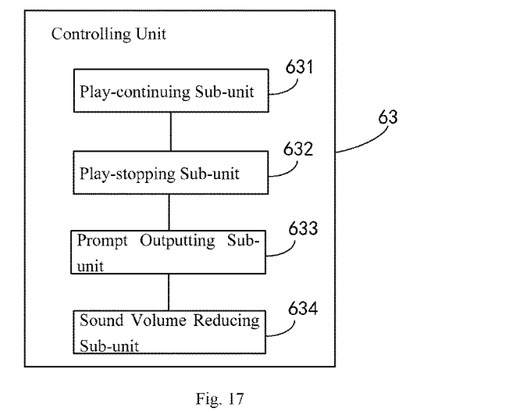
FIG. 17 is a block diagram showing a play control apparatus according to another exemplary embodiment of this disclosure.

As shown in FIG. 17, FIG. 17 is a block diagram showing a play control apparatus according to another exemplary embodiment of this disclosure. The controlling unit 63 may include a play-continuing sub-unit 631, a play-stopping sub-unit 632, a prompt outputting sub-unit 633 and a sound volume reducing sub-unit 634 based on the embodiment shown in FIG. 6.

The play-continuing sub-unit 631 is configured to continue playing preset data, if the brain wave information is the type identification of a β wave or an α wave.

The play-stopping sub-unit 632 is configured to stop playing the preset data, if the brain wave information is the type identification of a δ wave The prompt outputting sub-unit 633 is configured to output prompt information for changing the preset data, if the brain wave information is the type identification of any of a θ wave, a hump wave, a K-complex wave and a sleep spindle wave.

The sound volume reducing sub-unit 634 is configured to reduce a play sound volume of the preset data, if the brain wave information is the type identification of any of a θ wave, a hump wave, a K-complex wave and a sleep spindle wave.

When this embodiment of this disclosure is applied, by executing different play control for different types of brain waves, this disclosure can improve the flexibility of play control.

Figure 18:
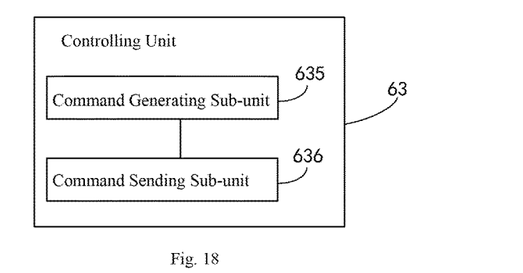
FIG. 18 is a block diagram showing a play control apparatus according to another exemplary embodiment of this disclosure.

As shown in FIG. 18, FIG. 18 is a block diagram showing a play control apparatus according to another exemplary embodiment of this disclosure. The controlling unit 63 may include a command generating sub-unit 635 and a command sending sub-unit 636 based on the embodiment shown in FIG. 6.

The command generating sub-unit 635 is configured to generate a control command corresponding with the brain wave information.

The command sending sub-unit 636 is configured to send the control command to an associated play device to trigger the play device to execute play response corresponding with the brain wave information.

If the brain wave information is the type identification of a δ wave, the control command is configured to stop playing preset data.

If the brain wave information is the type identification of any of a θ wave, a hump, a K-complex wave and a sleep spindle wave, the control command is configured to output prompt information for changing the preset data; or if the brain wave information is the type identification of any of a θ wave, a hump, a K-complex wave and a sleep spindle wave, the control command is configured to reduce the play sound volume of the preset data.

When this embodiment of this disclosure is applied, by generating a control command corresponding with the brain wave information and sending the control command to an associated play device to trigger the play device to execute play response corresponding with the brain wave information, this disclosure can execute play control for different play devices.

With respect to the apparatus in the above embodiments, the specific manners for performing operations for individual modules therein have been described in detail in the embodiments regarding the steps of the play control method, which will not be elaborated herein.

It is noted that the various modules, units and components in the present disclosure can be implemented using any suitable technology. In an example, a module can be implemented using integrated circuit (IC). In another example, a module can be implemented as a processing circuit executing software instructions.

Since the apparatus embodiments substantially correspond to the method embodiments, similar parts of the method embodiments may be referred to for the apparatus embodiments. The above apparatus embodiments are illustrative only. The units described as separate members may be or may not be physically separated. The members described as units may be or may not be physical units, may be located at the same place or may be distributed in multiple network units. The objectives of the solutions of this disclosure may be realized by selecting some or all of the modules according to the actual needs. The above can be understood and implemented by those skilled in the art without any inventive work.

Accordingly, this disclosure also provides a terminal, comprising: a processor; and a memory storing instructions executable by the processor, wherein the processor is configured to: acquire brain wave information of a target user; and execute play control corresponding with the brain wave information.

Figure 19:
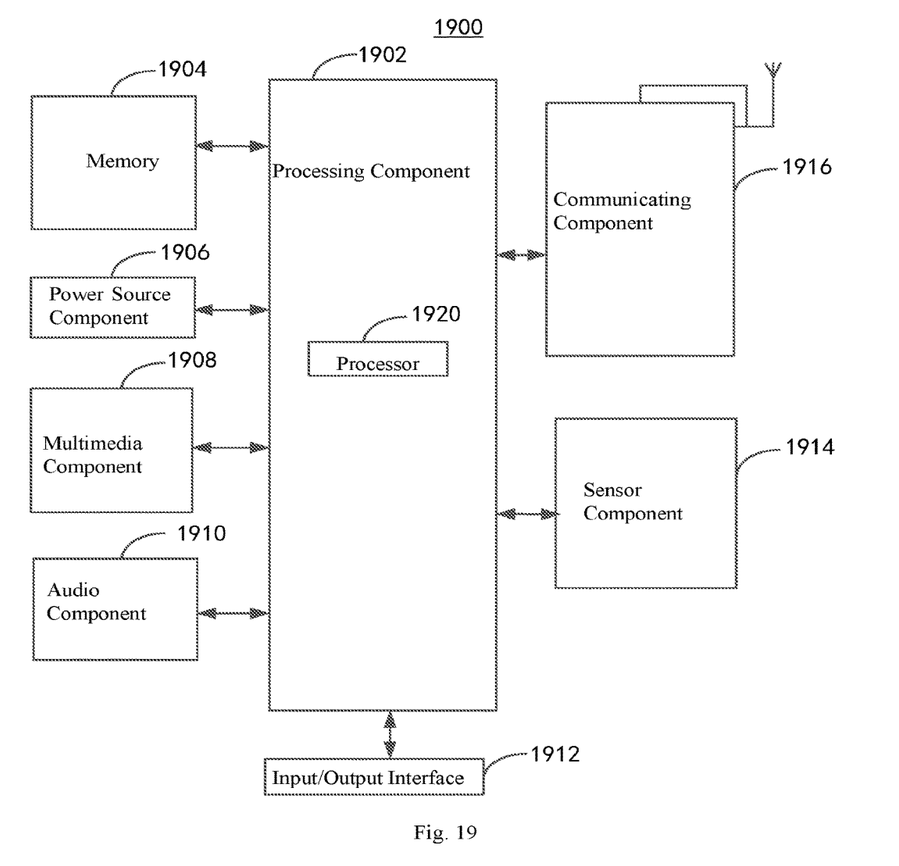
FIG. 19 is a schematic diagram showing a play control apparatus according to an exemplary embodiment of this disclosure.

FIG. 19 is a schematic diagram of a play control apparatus 1900 according to an exemplary embodiment. For example, the apparatus 1900 may be a mobile phone, a computer, a digital broadcast terminal, a messaging device, a gaming console, a tablet, a medical device, exercise equipment, a personal digital assistant or the like.

Referring to FIG. 19, the apparatus 1900 may include one or more of the following components: a processing component 1902, a memory 1904, a power component 1906, a multimedia component 1908, an audio component 1910, an input/output (I/O) interface 1912, a sensor component 1914, and a communication component 1916.

The processing component 1902 typically controls overall operations of the apparatus 1900, such as the operations associated with display, telephone calls, data communications, camera operations, and recording operations. The processing component 1902 may include one or more processors 1920 to execute instructions to perform all or part of the steps in the above described methods. Moreover, the processing component 1902 may include one or more modules which facilitate the interaction between the processing component 1902 and other components. For instance, the processing component 1902 may include a multimedia module to facilitate the interaction between the multimedia component 1808 and the processing component 1902.

The memory 1904 is configured to store various types of data to support the operation of the apparatus 1900. Examples of such data include instructions for any applications or methods operated on the apparatus 1900, contact data, phonebook data, messages, pictures, video, etc. The memory 1804 may be implemented using any type of volatile or non-volatile memory devices, or a combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

The power component 1906 provides power to various components of the apparatus 1900. The power component 1906 may include a power management system, one or more power sources, and any other components associated with the generation, management, and distribution of power in the apparatus 1900.

The multimedia component 1908 includes a screen providing an output interface between the apparatus 1900 and the user. In some embodiments, the screen may include a liquid crystal display (LCD) and a touch panel (TP). If the screen includes the touch panel, the screen may be implemented as a touch screen to receive input signals from the user. The touch panel includes one or more touch sensors to sense touches, swipes, and gestures on the touch panel. The touch sensors may not only sense a boundary of a touch or swipe action, but also sense a period of time and a pressure associated with the touch or swipe action. In some embodiments, the multimedia component 1908 includes a front camera and/or a rear camera. The front camera and the rear camera may receive an external multimedia datum while the apparatus 1900 is in an operation mode, such as a photographing mode or a video mode. Each of the front camera and the rear camera may be a fixed optical lens system or have focus and optical zoom capability.

The audio component 1910 is configured to output and/or input audio signals. For example, the audio component 1910 includes a microphone ("MIC") configured to receive an external audio signal when the apparatus 1900 is in an operation mode, such as a call mode, a recording mode, and a voice recognition mode. The received audio signal may be further stored in the memory 1904 or transmitted via the communication component 1916. In some embodiments, the audio component 1910 further includes a speaker to output audio signals.

The I/O interface 1912 provides an interface between the processing component 1902 and peripheral interface modules, such as a keyboard, a click wheel, buttons, and the like. The buttons may include, but are not limited to, a home button, a volume button, a starting button, and a locking button.

The sensor component 1914 includes one or more sensors to provide status assessments of various aspects of the apparatus 1900. For instance, the sensor component 1814 may detect an open/closed status of the apparatus 1900, relative positioning of components, e.g., the display and the keypad, of the apparatus 1900, a change in position of the apparatus 1900 or a component of the apparatus 1900, a presence or absence of user contact with the apparatus 1900, an orientation or an acceleration/deceleration of the apparatus 1900, and a change in temperature of the apparatus 1900. The sensor component 1914 may include a proximity sensor configured to detect the presence of nearby objects without any physical contact. The sensor component 1914 may also include a light sensor, such as a CMOS or CCD image sensor, for use in imaging applications. In some embodiments, the sensor component 1914 may also include an accelerometer sensor, a gyroscope sensor, a magnetic sensor, a pressure sensor, or a temperature sensor.

The communication component 1916 is configured to facilitate communication, wired or wirelessly, between the apparatus 1900 and other devices. The apparatus 1900 can access a wireless network based on a communication standard, such as WiFi, 2G, or 3G, or a combination thereof. In one exemplary embodiment, the communication component 1916 receives a broadcast signal or broadcast associated information from an external broadcast management system via a broadcast channel. In one exemplary embodiment, the communication component 1916 further includes a near field communication (NEC) module to facilitate short-range communications. For example, the NEC module may be implemented based on a radio frequency identification (RFID) technology, an infrared data association (IrDA)

technology, an ultra-wideband (UWB) technology, a Bluetooth (BT) technology, and other technologies.

In exemplary embodiments, the apparatus 1900 may be implemented with one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the above described methods.

In exemplary embodiments, there is also provided a non-transitory computer-readable storage medium including instructions, such as included in the memory 1804, executable by the processor 1920 in the apparatus 1900, for performing the above-described methods. For example, the non-transitory computer-readable storage medium may be a ROM, a RAM, a CD-ROM, a magnetic tape, a floppy disc, an optical data storage device, and the like.

Other embodiments of the invention will be apparent to those skilled in the art from consideration of the specification and practice of the invention disclosed here. This application is intended to cover any variations, uses, or adaptations of the invention following the general principles thereof and including such departures from the present disclosure as come within known or customary practice in the art. It is intended that the specification and examples be considered as exemplary only, with a true scope and spirit of the invention being indicated by the following claims.

It will be appreciated that the present invention is not limited to the exact construction that has been described above and illustrated in the accompanying drawings, and that various modifications and changes can be made without departing from the scope thereof. It is intended that the scope of the invention only be limited by the appended claims.

The invention claimed is:

1. A method for controlling an electronic device, comprising:
    detecting an object being in touch with a sensor device;
    determining whether the object is a user;
    acquiring brain wave information of the user who is associated with the electronic device when the object is determined to be the user; and
    controlling the electronic device based on the brain wave information,
    wherein
    the determining whether the object is the user comprises:
    receiving touch attributes of the object that is in touch with the sensor device;
    determining whether at least one of the touch attributes of the object meets a preset condition; and
    determining that the object that is in touch with the sensor device is the user when the at least one of the touch attributes meets the preset condition, and
    the determining whether the at least one of the touch attributes of the object meets the preset condition comprises:
    when a pressure of the object is detected by a built-in pressure sensor, an area of the object is detected by the built-in area sensor, and a ratio of the pressure to the area matches a preset density, determining that the detected pressure and area meet the corresponding preset condition.

2. The method according to claim 1, wherein acquiring the brain wave information of the user comprises: detecting the brain wave information of the user using a built-in brain wave sensor in the sensor device.

3. The method according to claim 2, wherein detecting the brain wave information of the user using the built-in brain wave sensor in the sensor device comprises:
    determining a contact position where the user is in touch with the sensor device; and
    detecting the brain wave information of the user using the built-in brain wave sensor that is selected from a plurality of built-in brain wave sensors in the sensor device, and is the closest to the contact position.

4. The method according to claim 1, wherein acquiring the brain wave information of the user comprises: receiving the acquired brain wave information of the user transmitted by a brain wave detector.

5. The method according to claim 1, wherein acquiring the brain wave information of the user comprises:
    acquiring at least one of a frequency, an amplitude and a waveform of brain wave parameters of the user; and
    determining a brain wave type corresponding to the acquired brain wave parameter as the brain wave information of the user.

6. The method according to claim 5, wherein determining the brain wave type corresponding to the acquired brain wave parameter as the brain wave information of the user comprises:
    retrieving the brain wave type corresponding to the acquired brain wave parameter from a first preset relationship table which records corresponding relationships between different brain wave parameters and brain wave types.

7. The method according to claim 1, wherein acquiring the brain wave information of the user comprises:
    acquiring at least one of a frequency, an amplitude and a waveform of brain wave parameters of the user;
    acquiring at least one of an age, a gender and a health state of physiological parameters of the user; and
    determining a brain wave type corresponding to the acquired brain wave parameter and the acquired physiological parameter as the brain wave information of the user.

8. The method according to claim 7, wherein determining the brain wave type corresponding to the acquired brain wave parameter and the acquired physiological parameter as the brain wave information of the user comprises:
    retrieving the brain wave type corresponding to the acquired brain wave parameter and the acquired physiological parameter from a second preset relationship table which records corresponding relationships among different brain wave parameters, physiological parameters and brain wave types.

9. The method according to claim 1, wherein controlling the electronic device based on the brain wave information comprises at least one of:
    when the brain wave information has a type identification of a β wave or an α wave, controlling the electronic device to continue a previous operation of preset data;
    when the brain wave information has the type identification of a δ wave, controlling the electronic device to stop the previous operation of preset data;
    when the brain wave information has the type identification of any of a θ wave, a hump wave, a K-complex wave and a sleep spindle wave, outputting prompt information for changing the preset data; and
    when the brain wave information has the type identification of any of a θ wave, a hump wave, a K-complex wave and a sleep spindle wave, reducing a sound volume.

10. The method according to claim 1, wherein controlling the electronic device based on the brain wave information comprises:
generating a control command based on the brain wave information; and
sending the control command to a media play device to trigger the media play device to execute a play response to the brain wave information,
wherein when the brain wave information has a type identification of a δ wave, the control command is used to control the media play device to stop playing preset data;
when the brain wave information has the type identification of any of a θ wave, a hump wave, a K-complex wave and a sleep spindle wave, the control command is used to control the media play device to output prompt information for changing the preset data; or
when the brain wave information has the type identification of any of a θ wave, a hump wave, a K-complex wave and a sleep spindle wave, the control command is used to control the media play device to reduce a play sound volume for playing the preset data.

11. A terminal device, comprising:
a processor; and
a memory storing instructions executable by the processor,
wherein the processor is configured to:
receive touch attributes of an object that is in touch with a sensor device;
determine whether at least one of the touch attributes of the object meets a preset condition;
determine that the object in touch with the sensor device is a user when the at least one of the touch attributes meets the preset condition;
acquire brain wave information of the user when the object is determined to be the user; and
control an electronic device associated with the user based on the brain wave information,
wherein the processor is further configured to perform:
when a pressure of the object is detected by a built-in pressure sensor, an area of the object is detected by the built-in area sensor, and a ratio of the pressure to the area matches a preset density, determining that the detected pressure and area meet the corresponding preset condition.

12. The terminal device according to claim 11, wherein the processor is also configured to:
determine a contact position where the user is in touch with a sensor device; and
detect the brain wave information of the user using a built-in brain wave sensor that is selected from a plurality of built-in brain wave sensors and is closest to the contact position in the sensor device.

13. The terminal device according to claim 11, wherein the processor is also configured to:
acquire at least one of a frequency, an amplitude and a waveform of brain wave parameters of the user; and
determine a brain wave type corresponding to the acquired brain wave parameter as the brain wave information of the user.

14. The terminal device according to claim 11, wherein the processor is also configured to:
acquire at least one of a frequency, an amplitude and a waveform of brain wave parameters of the user;
acquire at least one of an age, a gender and a health state of physiological parameters of the user; and
determine a brain wave type corresponding to the acquired brain wave parameter and the acquired physiological parameter as the brain wave information of the user.

15. The terminal device according to claim 11, wherein the processor is also configured to:
generate a control command corresponding with the brain wave information; and
send the control command to a media play device to trigger the media play device to execute a play response to the brain wave information,
wherein
when the brain wave information has a type identification of a δ wave, the control command is used to control the media play device to stop playing preset data;
when the brain wave information has the type identification of any of a θ wave, a hump wave, a K-complex wave and a sleep spindle wave, the control command is used to control the media play device to output prompt information for changing the preset data; or
when the brain wave information has the type identification of any of a θ wave, a hump wave, a K-complex wave and a sleep spindle wave, the control command is used to control the media play device to reduce a play sound volume for playing the preset data.

* * * * *